United States Patent [19]

Linnau et al.

[11] Patent Number: 5,371,007
[45] Date of Patent: Dec. 6, 1994

[54] METHOD OF PRODUCING LYS-PLASMINOGEN

[75] Inventors: Yendra Linnau; Ernst Hetzl, both of Vienna, Austria

[73] Assignee: Immuno Aktiengesellschaft, Vienna, Austria

[21] Appl. No.: 41,332

[22] Filed: Apr. 1, 1993

Related U.S. Application Data

[63] Continuation of Ser. No. 900,794, Jun. 22, 1992, abandoned, which is a continuation of Ser. No. 378,277, Jul. 11, 1989, abandoned.

Foreign Application Priority Data

Jul. 28, 1988 [AT] Austria .................. 1919/88

[51] Int. Cl.$^5$ .............. C12P 21/00; C12N 9/00; C12N 9/68
[52] U.S. Cl. .................. 435/217; 435/68.1; 435/183
[58] Field of Search ............ 435/183, 217, 68.1

[56] References Cited

PUBLICATIONS

Rickli et al. (1971) *Biochim Biophys. Acta*, 250, 447–451.
Claeys et al. (1973) *Thrombosis Res*, 3, 515–523.
P. Wallen and B. Wiman, *Biochim. Biophys. Acta*, 221, 20–30 (1970).
D. Collen et al, *Thromb. Res.*, 7, 515–529 (1975).
*Biochim. Biophys. Acta*, 342, 351 (1974).
*Chemical Abstracts*, vol. 105, 1986, 105:22249b, "Production of Lys–plasminogen in urokinase–activated human plasma," Yamamoto et al.
*Haemostatis*, A. Schoppmann, et al, "Production and Quality Assurance of Lys–Plasminogen Steam Treated", vol. 18, suppl. 1, pp. 157–163, 1988.
*Mammalian Biochem.*, Y. Makino, et al, "Conversion of Glu–Plasminogen to Lys–Plasminogen: Analysis by Immunoblotting", vol. 106, pp. 411, No. 106:117156d, 1987.
Fritz et al., *Arzneim-Forsch./Drug Res.* 33:479–494 (1983).
Claeys et al. *Biochemica and Biophysica Acta*, 342:351–359 (1974).
Badylak et al., *Thrombosis Research* 62:115–126 (1991).

*Primary Examiner*—Douglas W. Robinson
*Assistant Examiner*—Jon P. Weber
*Attorney, Agent, or Firm*—Burns, Doane, Swecker & Mathis

[57] ABSTRACT

To produce lys-plasminogen having a specific activity of at least 17.5 caseinolytic units/mg protein and at least 50 mymoles/g protein nitrogen as well as an electrophoretic purity of at least 90%, plasminogen from plasma, a plasminogen-containing fraction or a tissue culture is adsorbed on immobilized lysine for the purpose of purification, is eluted and is recovered from the eluate by a protein precipitating agent. A solution of the thus purified plasminogen is adjusted to a plasmin activity ranging between 0.005 and 0.2 mymoles/ml min relative to chromogenic substrate H-D-valyl-L-leucyl-L-lysine-p-nitroanilide dihydrochloride, is maintained at a temperature of from $+1°$ C. to $+20°$ C. for a period of from 6 to 60 hours in order to provoke an enzymatic-proteolytic conversion of plasminogen into lys-plasminogen, whereupon the enzymatic action is interrupted and lys-plasminogen is isolated.

5 Claims, 4 Drawing Sheets

FIG. 1A

FIG. 1B

```
   I  I  G  T  G  D  D  C  I  S  I  V  S  G  S  Q  N  V  Q  A  T  N  I  T  C  G  P  G  H  G  I  S  I  G  S  L  G  S  G  N
CTATTATTGGAACAGGTGATGATTGTATTCAATTGTTTCTGGATCTCAAATGTGCAGGTCATCCAGGTCATGGTCCAGGTCATGGTATAAGTATTGGAAAGCTTAGGATCTGGAAA
         850        860        870        880        890        900        910        920        930        940        950        960
   S  E  A  Y  V  S  N  V  T  V  N  E  A  K  I  I  G  A  E  N  G  V  R  I  K  T  H  Q  G  G  S  G  Q  A  S  N  I  K  F  L
ATTCAGAAGCTTATGTGTCTAATGTTACTGTAAATGAAGCCAAAATTATCGGTGCCGAAAATGGAGTTAGGATCAAGACTCATCAAGGAGGATCTGGACAAGCTAGCAACATCAAATTTC
         970        980        990       1000       1010       1020       1030       1040       1050       1060       1070       1080
   N  V  E  M  Q  D  V  K  Y  P  I  I  I  D  Q  N  Y  C  D  R  V  E  P  C  I  Q  Q  F  S  A  V  Q  V  K  N  V  V  Y  E  N
TGAATGTTGAAATGCAAGACGTTAAGTATCCCATAATTATAGACCAAAACTATTGTGATCGAGTTGAACCATGTATACAACAGTTTCAGCAGTTCAAGTGAAAATGTGGTATGAGA
         1090       1100       1110       1120       1130       1140       1150       1160       1170       1180       1190       1200
   I  K  G  T  S  A  T  K  V  A  I  K  F  D  C  S  T  N  F  P  C  E  G  I  H  E  N  I  N  L  V  G  E  S  G  K  P  S  E
ATATCAAGGGCAACAAGTGCAACAAAGTGGCCATAAAATTTGATTGCAGCACAAACTTTCCATGTGAAGGAATTCATGAGAATATAAATTTAGTAGGGGAAAGTGGAAAACCATCAG
         1210       1220       1230       1240       1250       1260       1270       1280       1290       1300       1310       1320
   A  T  C  K  N  V  H  F  N  N  A  E  H  V  T  P  H  C  T  S  L  E  I  S  E  D  E  A  L  L  Y  N  Y  *
AGGCTACGTGCAAAAATGTCCATTTTAACAATGCTGAACATGTTACACCACACTGTACTTCACTAGAAATTTCAGAGGATGAAGCTCTTTTGTATAATTATTAATTATACTATAGATCT
         1330       1340       1350       1360       1370       1380       1390       1400       1410       1420       1430       1440

TCAATATATAGCAGATATGATATCACAATAAACAAATCTATATCTATGTATTGAATAATTATTATGTACGGATTGAAGTTTTAATAAGACTACTATGTATTTCTATTTCTA
         1450       1460       1470       1480       1490       1500       1510       1520       1530       1540       1550       1560

GTCAAAAGTTTGACGGATTGTACTTTTTAATGTACAAAATAATAAAATGGTTATTTATATGAAAAAAAAAAA
         1570       1580       1590       1600       1610       1620       1630
```

FIG. 2A

FIG. 2B

```
Q  L  V  A  R  K  P  G  K  Y  Q  Q  N  H  V  I  A  Q  G  R  T  D  P  N  Q  A  T  G  T  S  I  Q  F  C  D  I  I  A  S  P
GCCAGTCGTAGCTAGAAAACCGGGTAAATACCAGCAAAACATGGTGATCGCACAAGGCAGGACGGACCCAAATCAGGCCACGGGGACATCAATTCAGTTTTGTGATATAGCAAGTC
    850       860       870       880       890       900       910       920       930       940       950       960
D  L  K  P  V  V  K  E  F  P  T  Y  L  G  R  P  H  K  K  Y  S  R  T  V  V  H  E  S  S  L  G  G  L  I  D  P  S  G  H  A
CTGACCCTAAAACCAGTCGTGAAAGAATTCCCAACATATCTTGGTCGTCCACATAAGAAATATTCAAGAACTGTAGTGCATGAATCATCATTGGGTCTGATCGATCCATCGGGGTTGGG
    970       980       990      1000      1010      1020      1030      1040      1050      1060      1070      1080
E  H  H  G  D  F  A  L  K  T  L  Y  Y  G  E  F  M  N  N  G  P  G  A  G  T  S  K  R  V  K  H  P  G  Y  H  V  I  T  D  P
CTGAGTGGCACGGGAGATTTTGCGTTAAAGACATTGTATTATGGTGAATTTATGAATAATGGACCTGGTGCTGGTACTAGTAAGCGTGTCAAGCATCCTGGCTATCATGTCATTACTGACC
   1090      1100      1110      1120      1130      1140      1150      1160      1170      1180      1190      1200
A  E  A  M  S  F  T  V  A  K  L  I  Q  G  G  S  H  L  R  S  T  D  V  A  Y  V  D  G  L  Y  D  Y  S  D  I  K  L  L  F  V
CCGCTGAAGCTATGTCATTCACTGTGGCTAAGCTAATCCAGGGCGGATCACATCTCAGGAGCACAGATGTTGCTACTGTGGCGTATGTGGATGGATTATATGATTATAGTGATATAAAATTACTCTTTG
   1210      1220      1230      1240      1250      1260      1270      1280      1290      1300      1310      1320
Y  V  T  R  H  L  *
TTTATGTAACAAGACATCTTAAAAGTTCAAAGTAAGTAGTAATATATCCATATGAAGTGCCACATGAGCAGAGCGGATTAAGTGTCTAAAGCATAACACAAACTCTAGT
   1330      1340      1350      1360      1370      1380      1390      1400      1410      1420      1430      1440

GTGACAAGCATTTACATGGCTCATTCCTTACTACTAAGTCGTCAATAAGTTCAGTTAAGGGGTTCATAAGGGGTTCATAAGTTAATATACGTATATATATTTATGTGGCGATAAAGCTGAACTGATGATG
   1450      1460      1470      1480      1490      1500      1510      1520      1530      1540      1550      1560

CTTTAATGTAATTATAGTTTTCTGAAAAGCATATGTTTTCCCTGATGTTTATGGTTGTGGGGTGGTTATGTGGGGTGGTATGTGAATATTAGGTTTGTGGGGTGGTTATGTGAATATTAGGTTATGATAAAAATATGCAAGATGAAAAAAAAAAAA
   1570      1580      1590      1600      1610      1620      1630      1640      1650      1660      1670      1680
```

METHOD OF PRODUCING LYS-PLASMINOGEN

This application is a continuation of application Ser. No. 07/900,794, filed Jun. 22, 1992, now abandoned, which is a continuation of application Ser. No. 07/378,277, filed Jul. 11, 1989, now abandoned.

The invention relates to a method of producing lys-plasminogen having a specific activity of at least 17.5 caseinolytic units/mg protein and at least 50 μmoles/g protein nitrogen as well as an electrophoretic purity of at least 90%, wherein plasminogen from plasma, a plasminogen-containing fraction or a tissue culture is adsorbed on immobilized lysine for the purpose of purification, is eluted and is recovered from the eluate by a protein precipitating agent.

Lys-plasminogen is a generic name used in the literature to denote proteolytically modified forms of native plasminogen (glu-plasminogen) which are obtained from the same by cleaving a polypeptide from the $NH_2$ terminal. As the N-terminal amino acids of the presently known species of lys-plasminogen, lysine, methionine and valine have been detected so far. Values of between 90,000 and 94,000 for glu-plasminogen and values of about 80,000 for lys-plasminogen have been indicated in the literature as the respective molecular weights.

With regard to the fibrinolytic behavior, lys-plasminogen differs from glu-plasminogen primarily in two respects: lys-plasminogen possesses a higher binding affinity to the fibrin networks of thrombi and can be activated to plasmin far more rapidly (e.g., by urokinase). Both properties increase the efficiency of fibrinolysis and are the reasons for lys-plasminogen preferably being used in thrombosis therapy.

The starting material for the recovery of lys-plasminogen is the Cohn fraction III of plasma or plasma itself. The processes described in the literature consist of a plurality of process steps, such as extraction, adsorption and precipitation steps. The cleavage of an N-terminal polypeptide chain and conversion into lys-plasminogen either is effected directly on isolated glu-plasminogen or takes place in the course of the isolation and purification steps on account of the proteolytic activity present.

P. Wallen and B. Wiman (Biochim. Biophys. Acta 221, 20–30 (1970)) isolated plasminogen by extracting a washed Cohn III precipitate and precipitating the extract with methanol and ammonium sulfate at pH 4.8. This product contains 0.5 to 1.9% spontaneous proteolytic activity due to plasmin contaminations. After the addition of aprotinin, further purification by means of gel filtration and adsorption/elution on an anion exchanger yields a plasminogen that predominantly exhibits glutamine as the N-terminal amino acid and has a spontaneous proteolytic activity of 0.1 to 0.3%. Processing without any addition of aprotinin gives rise to a product mixture having a spontaneous proteolytic activity of 4% and lysine, valine, but also methionine and glutamine as N-terminal amino acids.

E. E. Rickli and P. A. Cuendet (Biochim. Biophys. Acta 250, 447–451 (1971)) immobilized lysine on polyacrylamide gel, using this gel to isolate plasminogen from plasma. After washing with a phosphate buffer, elution takes place with a buffer containing 0.5 moles/l 6-aminocaproic acid. By adding ammonium sulfate, plasminogen is precipitated from the eluate and the dissolved precipitate is dialyzed against NaCl-Tris-lysine or phosphate-NaCl buffer. Only glutamine is detectable as N-terminal amino acid.

D. Collen et al. (Thromb. Res. 7, 515–529 (1975)) also describe the preparation of plasminogen by affinity chromatography with lyeine agarose from plasma or Cohn III precipitate with and without the addition of aprotinin. Thus, with aprotinin pure glu-plasminogen is recovered from plasma, whereas without aprotinin the product contains traces of proteins with lys and val as N-terminal amino acids. Without any addition of aprotinin, a preparation with a spontaneous proteolytic activity (induced by the plasmin present) of 0.1 to 1% was isolated from Cohn III precipitate. When adding 25,000 to 50,000 KIU aprotinin per kg Cohn III precipitate and 5 KIU/ml to the washing and eluting solutions, the spontaneous proteolytic activity was below 0.1%, the separation of glu- and lys-plasminogen was effected by ion exchange chromatography on DEAE Sephadex A-50.

H. Claeys et al. (Thromb. Res. 3, 515–523 (1973) and Biochim. Biophys. Acta, 342, 351 (1974)) extracted plasminogen from Cohn III precipitate with a phosphate buffer (0.1 mole/l, pH 7.4) containing 10 KIU aprotinin/ml. After adsorption on lysine agarose and washing with a phosphate buffer, elution takes place with a buffer containing 6-aminocaproic acid (0.2 moles/l) and aprotinin (20 KIU/ml). The thus isolated plasminogen had a spontaneous proteolytic activity of about 0.4% and, in addition to glu and lys, contained traces of val and met as N-terminal amino acids. When processing plasma according to the same technique, only glu is detected as N-terminal amino acid, the spontaneous proteolytic activity amounting to below 0.1%. Further purification is effected by gel filtration (Sephadex G-150) and ion exchange chromatography (DEAE-Sephadex A-50). When adding aprotinin (400 KIU/ml) prior to further purification, an end product is isolated even with Cohn III precipitate used as starting material, which end product exhibits a spontaneous proteolytic activity of below 0.1% and glu as N-terminal amino acid. The conversion of glu-plasminogen to lys-plasminogen is achieved by the authors by incubation with plasmin (plasminogen/plasmin 200:1 to 20:3) at 37° C. and is stopped by the addition of trichloroacetic acid or aprotinin.

All these methods have disadvantages, because either they are not suited for the large-scale isolation of lye-plasminogen comprising method steps, such as, e.g. gel filtration, or they must be performed at room temperature, thus involving the risk of bacterial contamination of the pharmaceutical preparation. Usually, these methods, moreover, give rise to preparations that contain plasmin and, thus, have a high portion of spontaneous proteolytic activity. This is exactly what is undesired from a therapeutical point of view, because, upon application of the preparations, it takes effect on proenzymes of the coagulation system, partially destroying the same and, thus, giving rise to undesired side react ions. Although this proteolytic activity may be inhibited, this will, in turn, result in the contamination of the formed inactive complexes of the preparations produced.

The invention aims at avoiding these disadvantages and has as its object to produce lys-plasminogen having a specific activity of at least 17.5 caseinolytic units per mg protein and at least 50 μmoles plasminogen per nitrogen as well as an electrophoretic purity of at least 90%, wherein plasminogen from plasma, a plasminogen-containing fraction or a tissue culture is adsorbed on immobilized lysine for the purpose of purification, is eluted and is recovered from the eluate by a protein precipitating agent.

According to the invention, this object is achieved in that a solution of the thus purified plasminogen is adjusted to a plasmin activity ranging between 0.005 and 0.2 μmoles/ml min, preferably 0.01 and 0.1 μmoles/ml min, relative to the chromogenic substrate H-D-valyl-L-leucyl-L-lysine-p-nitroanilide dihydrochloride, is maintained at a temperature of from +1° C. to +20° C., preferably of from +4° C. to +12° C., for a period of from 6 to 60 hours, preferably 15 to 50 hours, in order to provoke an enzymatic-proteolytic conversion of plasminogen into lys-plasminogen, whereupon the enzymatic action is interrupted and lys-plasminogen is isolated.

To adjust the plasmin activity in accordance with the invention, plasmatic enzymes of the group consisting of serine proteases may be used. They comprise plasmin and plasmin-like enzymes. A plasmin activity of 0.01 to 0.1 μmoles/ml min corresponds to a plasminogen/plasmin ratio of from 30,000:1 to 3,000:1. Hence it is apparent that the proteolytic conversion of glu-plasmingen into lys-plasminogen is effected with surprisingly small amounts of enzyme.

Preferably, the action of plasmin on plasminogen is interrupted by the addition of inhibitors.

By using extremely slight amounts of plasmatic enzyme, the method according to the invention also does with slight amounts of inhibitors to interrupt the enzymatic action. By the addition of, e.g., 10 to 200 KIU/ml aprotinin or 0.01 to 1.0 U/ml Cl-esterase inhibitor, the activity may be lowered to less than or equal to 0.03 μmoles/ml relative to Substrate S 2251. This value is sufficient to ensure the stability of the product during subsequent processing steps, such as filtration, freeze-drying and, if desired, heat treatment for the inactivation of possibly present bacteria or viruses.

To restrict the action of plasmin, also other inhibitors, such as alpha2-macroglobuline or alpha2-antiplasmin, may be used.

A favorable embodiment of the method according to the invention consists in that the action of plasmin on plasminogen is effected while carrying out dialysis.

A particularly favorable variant of the method according to the invention for producing heat-stable lys-plasminogen from blood plasma or blood plasma products, which has a specific activity of at least 17.5 caseinolytic units per mg protein, at least 50 nmoles plasminogen per mg nitrogen as well as an electrophoretic purity of at least 90%, is characterized by the combination of the following measures:

a) extracting a Cohn fraction III (precipitate) by means of a phosphate buffer in the presence of 0.1 to 100 KIU aprotinin per ml buffer solution in order to obtain a crude plasminogen fraction, b) treating the crude plasminogen fraction with ethanol in order to precipitate the main portion of non-plasminogen proteins from the extract and eliminate the same, c) isolating plasminogen from the ethanolic solution by adsorption on immobilized lysine and subsequent elution, d) precipitating the thus purified plasminogen by means of ammonium sulfate or polyethylene glycol (PEG) and centrifuging the same, e) dissolving the precipitate and dialyzing the solution in the presence of plasmin, the solution having a plasmin activity of from 0.01 to 0.1 μmoles/ml min relative to chromogenic substrate S 2251, then f) interrupting the enzymatic action by adding 10 to 200 KIU aprotinin, and g) lyophilizing the solution and, if desired, heat-treating the lyophilisate.

This embodiment, thus, departs from a Cohn fraction III (precipitate), an extract being initially produced from this fraction with a phosphate buffer. This extract contains large amounts of inert accompanying proteins, such as, e.g., immunoglobulins and lipoproteins, the latter, in particular, rendering difficult the purification by means of affinity chromatography on immobilized lysine, due to poor filtration properties and unspecific interactions.

By precipitation with ethanol, the major portion of these disturbing accompanying proteins can be eliminated.

On account of the presence of 0.1 to 100 KIU aprotinin/ml buffer solution, the stability of plasminogen is safeguarded during affinity chromatographic purification. As the matrix for affinity chromatography, a gel containing lysine as the ligand, preferably a lysine-polyacryl amide gel, is used. After adsorption, the remaining accompanying proteins are removed by washing—preferably by means of a phosphate buffer—and subsequently plasminogen is eluted. This affinity chromatographic purification may be carried out either on a column or in a batch process.

By treating the eluate with protein precipitating agents, such as, e.g., ammonium sulfate or polyethylene glycol 4000, an intermediate product is precipitated that corresponds to glu-plasminogen described in the literature in terms of its properties and, in SDS PAGE, has a molecular weight of 92,000.

This intermediate product is capable of being converted into a fibrinolytic proenzyme already with extremely slight amounts of plasmin, which proenzyme exhibits the properties of lys-plasminogen described in the literature and, in SDS-PAGE, has a molecular weight of 84,000.

By optionally adding plasmin or aprotinin, the proteolytic activity of the solution of purified plasminogen (glu-plasminogen) may be increased or lowered such that the above-defined range of preferably 0.01 to 0.1 μmoles/ml min will be very easily adjustable in this manner. The enzymatic action within the solution is interrupted after the conversion with aprotinin, the solution is lyophilized and, if desired, the lyophilisate is heat-treated.

The procedures necessary to carry out the method according to the invention will be explained in more detail in the following.

Determination of the spontaneous proteolytic activity with chromogenic substrate H-D-valyl-L-leucyl-L-lysine-p-nitroanilide dihydrochloride (S 2251, Kabi):

The principle consists in that plasmin and other proteolytic enzymes cleave from the chromogenic substrate p-nitroaniline, whose liberation is measurable spectrophotometrically as the increase in extinction at 405 nm.

At first, the samples are pre-diluted at ratios of 1:2, 1:5, 1:10 and 1:20, to which end an aqueous solvent having pH=7.2 and containing 10 mmoles/l lysine, 0.5% by weight PEG 6000 and 50% by weight glycerol is used.

The chromogenic substrate is dissolved to a concentration of 5 mmoles/l in distilled water. An aqueous solution of pH=7.2 containing 50 mmoles/l Tris and 180 mmoles/l NaCl serves as the test buffer.

For assaying, 0.25 ml sample dilution is mixed with 0.55 ml test buffer, is incubated at 37° C., and, upon the addition of 0.05 ml substrate solution, the increase in the extinction at 405 nm is observed at a temperature of 37° C. The calculation of the activity is based on the formula $$E/min.0.321.\text{dilution factor} = \mu\text{moles/ml min}$$

Determination of the specific activity of plasminogen:

a) Caseinolytic units (CU)/mg protein

By reaction with streptokinase, plasminogen is activated to plasmin, which cleaves casein fragments that are soluble in trichloroacetic acid and are detectable by spectrophotometric measurement of the extinction at 280 nm in the supernatant.

The pre-dilution of the samples to an activity of 0.5 to 2.5 CU/ml is effected with an aqueous solution of pH=9.0, containing 50 mmoles/l Tris, 20 mmoles/l lysine, 0.1 moles/l NaCl and 1 mmoles/l EDTA.

The substrate is produced by dissolving casein according to Hammarsten (4%) in a phosphate buffer (67 mmoles/l, pH 7.4).

For activation, a solution of streptokinase (2500 IU/ml) in phosphate buffer as above is used.

To effect assaying 2.0 ml casein solution, 1.4 ml phosphate buffer (67 mmoles/l, pH 7.4), 0.4 ml sample dilution and 0.2 ml streptokinase solution are mixed in an ice-bath, buffer being pipetted instead of the sample dilution for the blank. After heating to 37° C. for 30 minutes, the samples are again placed into the ice-bath and the non-cleaved casein is precipitated by the addition of 6 ml 15% trichloroacetic acid. After standing for at least 30 minutes at room temperature, filtration over folded filters takes place and the extinction in the supernatant is measured at 280 nm relative to the blank.

The calculation of the caseinolyic activity is effected according to the formula $$E_{280}.16.3\text{dil.} = CU/ml.$$

Double assays are each made of at least two different dilutions being within the measuring range.

The conversion into the specific activity (CU/mg protein) is effected by dividing the caseinolytic activity by the protein value (Kjeldahl, in mg/ml).

b) Micromole plasminogen/g protein nitrogen

This assay method is known as "active site cross titration". At first, plasminogen is activated by complex formation with streptokinase. This complex reacts with p-nitrophenol-p'-guanidino benzoate under liberation of p-nitrophenol, which is determined spectrophotometrically by measuring the extinction at 400 nm.

The following reagents are used:

| | |
|---|---|
| Test buffer (pH = 7.7): | 100 mmoles/1 Na₂HPO₄ |
| | 1 mmole/1 6-aminocaproic acid |
| Streptokinase buffer: | 30 mmoles/1 Na₂HPO₄ |
| | 150 mmoles/1 Na glutamate |
| Titration solution: | 2.5 mmoles/1 p-nitrophenyl-p'-guanidino benzoate in dry DMSO (dried over molecular sieve 0.4 nm) |
| Standard solution: | 1.0 mg p-nitrophenol per 1 ml in dry DMSO. Prior to utilization, 5 ml are |

-continued

| |
|---|
| diluted with dry DMSO to 100 ml. |

For assaying, ml test buffer, 50 μl streptokinase solution (about 200 nmoles/ml) and "V" μl sample are incubated at 25° C. for 20 to 30 min, the extinction being measured at 400 nm for 2.5 minutes. After the addition of 20 μl titration solution, it is mixed, the extinction again being observed at 400 nm. The increase in extinction measured after the addition of the titration solution, which is to range between 0.08 and 0.12, is entered into the calculation as "At".

Blank run: Instead of streptokinase, streptokinase buffer and, instead of the sample, an equal volume of a buffer having the same salt composition as the sample are added, otherwise the procedure is the same as in the test run. The increase in extinction is entered in the calculation as "Ab".

Standard run: Procedure as in the blank run, yet instead of the titration solution, a standard solution is added. The increase in extinction is entered in the calculation as "As".

The calculation of the plasminogen activity is effected according to the formula $$\frac{(At - Ab) \cdot 20 \cdot 0.00036 \cdot 10^6}{As \cdot V} = \mu\text{moles/l}$$

Dividing this activity by the content of the solution of protein nitrogen (Kjeldahl, in g/l) yields the specific activity of plasminogen in μmole/g protein nitrogen.

Determination of the molecular weight (SDS polyacrylamide gel electrophoresis, SDS PAGE):

This method consists in that proteins are uniformly charged by the addition of SDS and migrate according to their molecular sizes in polyacrylamide gel when applying electric potential. By comparing the migration distance with that of calibration proteins of known molecular weights, the molecular weight of the samples to be assayed can be determined.

To carry out the method, 47.5 g acrylamide and 2.5 g N,N-methylene-bis-acrylamide are dissolved in an aqueous buffer solution of pH 7.1 containing 6 moles/l urea, 0.1 moles/l Tris and 0.1% SDS (sodium dodecyl sulfate).

57 ml of this solution, 3 ml of a 0.5% aqueous ammonium peroxo disulfate solution and 90 myl N,N,N',N'-tetramethyl ethylenediamine are rapidly mixed and filled into a gel casting stand. After polymerization, the gel is used in an electrophoresis apparatus. The samples are diluted to a protein concentration of 2.5 mg/ml with a solution containing 9 moles/l urea and 4.5% SDS. After further dilution (1+1) with glycerol bromphenol blue, 6 μl sample are each applied. A buffer of pH=7.1 containing 0,1 mole/l Tris, 0.1% SDS and 0.001% sodium azide is used for electrophoresis. The electrophoresis is performed for 10 min at 50 V and subsequently for 3 h at 100 V. Then the gel is stained with a solution of 2 g Coomassie blue in 455 ml methanol, 455 ml water and 90 ml glacial acetic acid for one hour at room temperature. Destaining is effected by a mixture of 2.5 l methanol, 1.0 l glacial acetic acid and 6.5 l water.

To determine the molecular weight, the migration distances are measured, the latter being proportional to the logarithm of the molecular weight. From a parallelly analyzed calibrator, a calibration line is, thus, established, from which the molecular weight of the samples to be investigated may be read.

If several protein bands are to be recognized in the samples to be investigated, their distribution will be determined by densitometric evaluation of the extinction at 601 nm.

Preparation of lysine polyacrylamide gel:

100 g Biogel P-300 (150–300 μm, polyacrylamide gel of Bio-Rad) are swelled in 2.6 l water for 2 h at 47° C. and are converted into the hydrazide by reaction with 1.2 l hydrazine hydrate during 20 h at 47° C. It is washed with distilled water until a pH of below 8.5 is reached (filtration over Büchner funnels). The washed gel is suspended in 6 l 0.3N HCl and the pH is corrected to 1.1. After cooling to 0° C., a cold solution of 56 g sodium nitrite in 200 ml water is added and stirred for 3 min. After the addition of a solution of 730 g lysine in 2 l water, it is stirred for at least 3 h at a temperature of not greater than +4° C. and at a pH of 9.5. Subsequently, stirring is continued for further 16 h at +4° C. After washing three times with 20 l water each and filtration over Büchner funnels, it is stirred with 15 l of a solution containing 107 g/l ammonium chloride (pH=8.8) for 16 to 20 h at +4° C. Then the gel is washed with water and afterwards with a phosphate buffer.

The method according to the invention will be further explained by way of the following examples.

EXAMPLE 1

1 kg Cohn III precipitate was suspended at 0° C. in 10 l of a phosphate buffer pH 7.4 to which 10 KIU/ml aprotinin had previously been added. Under cooling to −2° C., ethanol was added until a final concentration of 10%. After 15 hours of stirring at a temperature of −2° C., it was centrifuged and the supernatant was filtered over a depth filter based on cellulose (AMF Cuno Zeta Plus 50 S). Subsequently, it was diluted with 5 l phosphate buffer and 500 g lysine polyacrylamide gel were introduced. After a stirring time of one hour at 0° C., the gel loaded with plasminogen was separated by filtration over Büchner funnels and washed with a phosphate buffer several times until no more protein was detectable in the filtrate. By stirring with a solution of 6-aminocaproic acid (0.1 moles/l) in phosphate buffer, plasminogen was eluted and subsequently precipitated by the addition of 261 g ammonium sulfate per kg eluate.

The precipitate obtained by centrifugation was dissolved in 32 ml of an isotonic phosphate/saline buffer. Since further processing of the preparation according to the invention depends on the presence of a plasmatic enzyme, i.e., plasmin, having the activity indicated, the plasmin activity of the solution relative to chromogenic substrate S 2251 was measured at first. It amounted to 0.045 μmoles/ml so that no correctional adjustment was necessary in that case. In SDS PAGE only one band at a molecular weight of 92,000 (=glu-plasminogen) was detectable prior to carrying out the subsequently intended dialysis.

After dialysis against an isotonic phosphate/saline solution for 36 h at a temperature of 5.0° C., 50 KIU/ml aprotinin were added. The activity relative to substrate S 2251 amounted 0.01 μmoles/ml min at that time. The test for caseinolytic activity revealed 342 CU/ml. With a protein content of 15.6 g/l (according to Kjeldahl), this corresponds to a specific activity of 21.9 CU/mg. The active site cross titration revealed an activity of 164 μmoles/l and, hence, a specific activity of 65.7 μmoles/g protein nitrogen. During dialysis, the conversion of the protein having a molecular weight of 92,000 (glu-plasminogen) into a protein having a molecular weight of 84,000 (lys-plasminogen) was detecable in SDS PAGE. The portion of this product was 98%.

After the addition of 20 mmoles/l lysine, a pH of 7.0 was adjusted, then filtration and freeze-drying were carried out. The water content of the lyophilisate was brought to 7.8% by weight, and subsequently it was heated to 60° C. for 10 h to inactivate possibly present bacteria or viruses. After dissolution in distilled water, it was sterile-filtered, sterile-filled and again freeze-dried. In the tests for specific activity and electrophoretic purity, the thus obtained final product showed unaltered results compared to the product obtained immediately upon dialysis.

EXAMPLE 2

The extraction of Cohn III precipitate, ethanol precipitation and filtration were carried out as in Example 1. After dilution with phosphate buffer, the solution was pumped through a chromatographic column packed with 100 g lysine polyacrylamide gel. Washing and elution were performed with the solutions described in Example 1, but in the chromatographic column. Precipitation from the eluate with ammonium sulfate and dissolution of the precipitate were effected as in Example 1. In SDS PAGE only one band at a molecular weight of 92,000 was detected. The activity relative to chromogenic substrate S 2251 amounted to 0.003 μmole/ml min. By adding plasmin, it was increased to 0.016 μmole/ml min. After dialysis for 43 h at 7° C. and subsequent addition of 100 KIU/ml aprotinin, the portion of the band at a molecular weight of 84,000 (=lys-plasminogen) was found to be more than 98% in SDS PAGE. The specific activity amounted to 22.3 CU/mg protein and 60.5 μmoles/g nitrogen, respectively.

EXAMPLE 3

The extraction of Cohn III precipitate with phosphate buffer was carried out after the addition of 2 KIU/ml aprotinin. Further processing until precipitation with ammonium sulfate and dissolution of the precipitate were effected as in Example 2.

The activity of the solution relative to chromogenic substrate S 2251 amounted to 0.014 μmole/ml min. After dialysis for 22 h at a temperature of 11.7° C. and subsequent addition of 20 KIU/ml aprotinin, a specific activity of 20.5 CU/mg protein and 56.3 μmole/g protein nitrogen, respectively, was found, the portion of lys-plasminogen in SDS PAGE was 96%.

EXAMPLE 4

The isolation of plasminogen until the elution of lysine polyacrylamide gel was effected as described in Example 3. By the addition of 70 g polyethylene glycol 4000 to 350 ml eluate, plasminogen was precipitated. The precipitate obtained by centrifugation was dissolved in 15 ml of a phosphate/NaCl buffer; in SDS PAGE only "glu-plasminogen" having a molecular weight of 92,000 was detectable. After the addition of plasmin, the activity measured with substrate S 2251 amounted to 0.01 μmole/ml min; dialysis took place for 42 hours at a temperature of 6.6° C., subsequently aprotinin (50 KIU/ml) was added.

The portion of lys-plasminogen in SDS PAGE was 95%; a specific activity of 23.4 CU/mg protein and of 59.0 μmole/g protein nitrogen, respectively, was determined.

What we claim is:

1. A method of producing lys-plasminogen having a specific activity of at least 17.5 caseinolytic units/mg protein and at least 50 μmols/g protein nitrogen as well as an electrophoretic purity of at least 90% comprising the steps of:
   (i) adsorbing plasminogen from plasma, a plasminogen-containing fraction or a tissue culture on immobilized lysine for the purpose of purification;
   (ii) eluting said plasminogen;
   (iii) precipitating said plasminogen from the eluate;
   (iv) dissolving the precipitated plasminogen to obtain a solution containing plasminogen and trace amounts of plasmin activity;
   (v)(a) if the plasmin activity is between 0.005 and 0.2 μmol/ml min relative to chromogenic substrate H-D-valyl-L-leucyl-L-lysine-p-nitroanilide dihydrochloride, plasminogen solution is maintained at a temperature of from +1° C. to +20° C. for a period of from 6 to 60 hours in order to provoke an enzymatic-proteolytic conversion of said plasminogen into lys-plasminogen;
   (v)(b) if the plasmin activity is below 0.005 μmol/ml min relative to said chromogenic substrate, plasmin is added to obtain a plasmin activity between 0.005 and 0.2 μmol/ml min relative to said chromogenic substrate and plasminogen solution is maintained at a temperature of from +1° C. to 20° C. for a period of from 6 to 60 hours in order to provoke an enzymatic-proteolytic conversion of said plasminogen into lys-plasminogen; or
   (v)(c) if the plasmin activity is above 0.2/μmol/ml min relative to said chromogenic substrate, plasmid inhibitor is added to obtain a plasmin activity between 0.005 and 0.2 μmol/ml min relative to said chromogenic substrate and the plasminogen solution is maintained at a temperature of from +1° C. to 20° C. for a period of from 6 to 60 hours in order to provoke an enzymatic-proteolytic conversion of said plasminogen into lys-plasminogen;
   (vi) interrupting the enzymatic action with a plasmin inhibitor; and
   (vii) isolating said lys-plasminogen.

2. The method of claim 1, wherein said plasmin activity ranges between 0.01 and 0.1 μmole/ml min, said temperature ranges from +4° C. to +12° C. and said period of time ranges from 15 to 50 hours.

3. The method of claim 1, wherein said plasmin inhibitor is selected from the group consisting of aprotinin in an amount of from 10 to 200 KIU/ml, Cl-esterase inhibitor in an amount of from 0.01 to 1.0 U/ml, alpha2-macroglobulin and alpha2-antiplasmin.

4. The method of claim 1, wherein said plasmin activity is allowed to act on said plasminogen while carrying out dialysis.

5. The method of claim 1 wherein said plasmin activity ranges between 0.01 and 0.1 μmol/ml min.

* * * * *

UNITED STATES PATENT AND TRADEMARK OFFICE
CERTIFICATE OF CORRECTION

PATENT NO. : 5,371,007
DATED : December 6, 1994
INVENTOR(S) : Yendra LINNAU, et al.

It is certified that error appears in the above-indentified patent and that said Letters Patent is hereby corrected as shown below:

On the cover page, please delete "4 Drawing Sheets".

Please delete "FIGS. 1A, 1B, 2A, and 2B."

Signed and Sealed this

Ninth Day of May, 1995

Attest:

BRUCE LEHMAN

Attesting Officer     *Commissioner of Patents and Trademarks*